United States Patent
Batchelor et al.

(10) Patent No.: US 9,980,892 B2
(45) Date of Patent: May 29, 2018

(54) SKIN CARE COMPOSITION

(71) Applicant: Conopco, Inc., Englewood Cliffs, NJ (US)

(72) Inventors: Stephen Norman Batchelor, Chester (GB); Peter Fairley, Chester (GB); Naresh Dhirajlal Ghatlia, Shanghai (CN); Adam John Limer, Northwich (GB); Xuezhi Tang, Shanghai (CN); Jian-Rong Zhang, Shanghai (CN)

(73) Assignee: Conopce, Inc., Englewood Cliffs, NJ (US)

( * ) Notice: Subject to any disclaimer, the term of this patent is extended or adjusted under 35 U.S.C. 154(b) by 0 days. days.

(21) Appl. No.: 15/303,026

(22) PCT Filed: Mar. 10, 2015

(86) PCT No.: PCT/EP2015/054878
§ 371 (c)(1),
(2) Date: Oct. 10, 2016

(87) PCT Pub. No.: WO2015/158465
PCT Pub. Date: Oct. 22, 2015

(65) Prior Publication Data
US 2017/0027834 A1 Feb. 2, 2017

(30) Foreign Application Priority Data

Apr. 14, 2014 (WO) ................. PCT/CN2014/075299
May 27, 2014 (EP) ..................................... 14170003

(51) Int. Cl.
*A61K 8/49* (2006.01)
*A61Q 1/02* (2006.01)
*A61K 8/84* (2006.01)
*A61K 8/73* (2006.01)
*A61K 8/64* (2006.01)
*A61K 8/81* (2006.01)
*A61K 8/87* (2006.01)
*A61Q 19/02* (2006.01)
*A61Q 19/04* (2006.01)

(52) U.S. Cl.
CPC .......... *A61K 8/4926* (2013.01); *A61K 8/4966* (2013.01); *A61K 8/64* (2013.01); *A61K 8/73* (2013.01); *A61K 8/731* (2013.01); *A61K 8/733* (2013.01); *A61K 8/8152* (2013.01); *A61K 8/84* (2013.01); *A61K 8/87* (2013.01); *A61Q 1/02* (2013.01); *A61Q 19/02* (2013.01); *A61Q 19/04* (2013.01); *A61K 2800/432* (2013.01)

(58) Field of Classification Search
CPC ........ A61K 8/4966; A61K 8/731; A61K 8/87; A61K 8/8152; A61K 8/64; A61K 8/4926; A61K 8/84; A61K 8/73; A61K 2800/00; A61Q 1/02; A61Q 19/04; A61Q 19/02
See application file for complete search history.

(56) References Cited

U.S. PATENT DOCUMENTS

| 3,679,347 A | 7/1972 | Brown |
| 4,182,612 A * | 1/1980 | Sokol ............... A61K 8/355 525/359.2 |
| 5,192,332 A | 3/1993 | Lang et al. |
| 5,972,359 A | 10/1999 | Sine et al. |
| 5,997,890 A | 12/1999 | Sine et al. |
| 6,174,533 B1 | 1/2001 | SaNogueira, Jr. et al. |
| 6,855,681 B1 * | 2/2005 | Ness ............... B01J 13/02 510/101 |
| 2005/0019509 A1 * | 1/2005 | Gardner ............ B29C 41/14 428/34.1 |
| 2005/0050656 A1 | 3/2005 | Huang et al. |
| 2009/0151087 A1 * | 6/2009 | Mario ............... A61K 8/22 8/406 |
| 2010/0247459 A1 * | 9/2010 | Drovetskaya ....... A61K 8/0208 424/59 |
| 2013/0152608 A1 * | 6/2013 | Wray ............... F16L 55/1003 62/50.7 |

FOREIGN PATENT DOCUMENTS

| EP | 0951276 | 6/2002 |
| EP | 1489144 | 12/2004 |
| KR | 1020080060480 | 7/2008 |
| WO | WO9826753 | 6/1998 |
| WO | WO9852535 | 11/1998 |
| WO | WO2004103335 | 2/2004 |
| WO | WO2007021731 | 2/2007 |
| WO | WO2009030344 | 3/2009 |
| WO | WO2009090125 | 7/2009 |
| WO | WO2011038022 | 3/2011 |
| WO | WO201113680 | 9/2011 |
| WO | WO2012098046 | 7/2012 |
| WO | WO 2012/119820 A2 * | 9/2012 |
| WO | WO2012119810 | 9/2012 |
| WO | WO2012119821 | 9/2012 |
| WO | WO2012126665 | 9/2012 |
| WO | WO2012126987 | 9/2012 |
| WO | WO2012130492 | 10/2012 |
| WO | WO 2013/074860 A1 * | 5/2013 |
| WO | WO2013074860 | 5/2013 |
| WO | WO2015158467 | 10/2015 |

OTHER PUBLICATIONS

Gu et al, Preparation and colloidal stability of monodisperse magnetic polymer particles, Journal of Colloid and Interface Science, 2005, pp. 419-426, vol. 289, CN.
IPRP in PCTEP2015054878, dated Apr. 20, 2016.
IPRP2 in PCTEP2015054887, dated Jun. 30, 2016.

(Continued)

*Primary Examiner* — Blessing M Fubara
(74) *Attorney, Agent, or Firm* — Edward A. Squillante, Jr.

(57) ABSTRACT

A skin care composition is described comprising water-soluble dye polymer comprising polymer backbone having negatively charged reactive dye substituent covalently bound thereto; and cosmetically acceptable carrier. The dye polymer is present in amount of 0.00001 to 0.1% in terms of reactive dye substituent by weight of the skin care composition. The composition is useful for providing cosmetic benefits such as skin lightening, evening skin tone and masking blemishes.

11 Claims, No Drawings

(56) References Cited

OTHER PUBLICATIONS

Search Report and Written Opinion in EP14170002, dated Nov. 19, 2014.
Search Report and Written Opinion in EP14170003, dated Nov. 19, 2014.
Search Report and Written Opinion in PCTEP2015054878, dated Apr. 7, 2015.
Search Report and Written Opinion in PCTEP2015054887, dated May 15, 2015.
Written Opinion 2 in PCTEP2015054887, dated Apr. 29, 2016.

* cited by examiner

SKIN CARE COMPOSITION

FIELD OF THE INVENTION

The present invention relates to skin care compositions comprising water-soluble dye polymers. More particularly the present invention relates to such compositions wherein the dye polymer comprises polymer backbone having negatively charged reactive dye substituent covalently bound thereto.

BACKGROUND OF THE INVENTION

Cosmetic compositions of various kinds are widely used by consumers. Skin care cosmetics such as moisturizing lotions or creams are applied to obtain benefits of anti-aging, skin lightening and moisturizing, while make-up cosmetic products are applied to obtain desired optics and color benefits.

There is increasing interest in cosmetic compositions which provide skin care benefits such as moisturization but which at the same time are capable of altering skin appearance. Unlike make-up compositions, however, the desire from skin care compositions is to enhance existing skin tones or at least to provide effects that are not perceived as unnatural. To this end colourants, such as pigments or dyes, are sometimes added to cosmetic compositions.

Pigment particles have the disadvantage that their presence can lead to an undesired poor tactile sensory property. Small molecule dyes have the disadvantage of being permeable to skin and so their use is highly regulated to avoid unwanted toxicity or adverse reactions. Furthermore both pigments and dyes when used in the low quantities required to give colouring without unnatural skin tone can be easily washed and/or rubbed from the skin after application resulting in only short-lived effects.

Thus the present inventors have recognized a need to provide cosmetic compositions capable of providing skin care benefits, but which do not have one or more of the drawbacks mentioned above.

SUMMARY OF THE INVENTION

In a first aspect, the present invention is directed to a skin care composition comprising:
  a) water-soluble dye polymer comprising polymer backbone having negatively charged reactive dye substituent covalently bound thereto; and
  b) cosmetically acceptable carrier;
    wherein the dye polymer is present in amount of 0.00001 to 0.1%, preferably 0.001 to 0.1%, in terms of reactive dye substituent by weight of the skin care composition.

In a further aspect the present invention is directed to use of the dye polymer or the composition according to any embodiment of the first aspect for delivering a cosmetic benefit selected from providing or enhancing natural skin tone, providing or enhancing pinkish appearance, or a combination thereof. The dye polymer or the composition may additionally or alternatively deliver one of the aforementioned cosmetic benefits in a durable manner.

All other aspects of the present invention will more readily become apparent upon considering the detailed description and examples which follow.

DETAILED DESCRIPTION

Except in the examples, or where otherwise explicitly indicated, all numbers in this description indicating amounts of material or conditions of reaction, physical properties of materials and/or use may optionally be understood as modified by the word "about".

All amounts are by weight of the skin care composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

The dye polymers of the present invention are water-soluble. By "water-soluble" is meant that the polymer is soluble in water at pH 7, 1 atm and 25° C. to give a solution with a concentration of at least 0.005% polymer (backbone+substituent) by weight of the solution, preferably at least 0.01%, most preferably from 0.1 to 10%.

The dye polymer comprises polymer backbone having negatively charged reactive dye substituent covalently bound thereto.

The polymer backbone is typically derived from a polymer containing one or more groups selected from alcohol (C—OH), thiol (C—SH), primary amine (C—NH$_2$), secondary amine (C—NH—C), or a combination thereof. Such groups are especially suitable for reaction with the reactive dye to form the covalent bond(s).

Suitable backbones include those derived from synthetic polymers such as polyvinylalcohol, polyethyleneimine, polypropyleneimine, polyvinylamine; polyetheramine, polyvinylimine, aminosilcone, polyurethane, cationic modified celluloses, and cationic modified polyvinylalcohol. Also suitable are backbones derived from cationic polymers having the INCI designation Polyquaternium such as Polyquaternium-4 (Hydroxyethyl cellulose dimethyl diallylammonium chloride copolymer) or Polyquaternium-37 (Poly (2-methacryloxyethyltrimethylammonium chloride)). Most preferred is polyurethane, Polyquaternium-4, or a mixture thereof. In some embodiments the polymer is preferably derived from a polymer other than a polyethylene imine.

The weight average molecular weight (as measured, for example using gel permeation chromatography) of the dye-polymer is preferably between 1,000 and 5,000,000 g mol$^{-1}$, more preferably between 5,000 and 1,000,000.

The dye-polymer backbone preferably carries quaternary ammonium groups or protonated amine groups.

Preferable the dye-polymer backbone before reaction with the reactive dye contains at least 1 OH, NH or NH$_2$ groups, more preferably at least 10 groups selected from OH, NH, NH$_2$, or a mixture thereof most preferably per 1000 molecular weight of the dye-polymer backbone before reaction there is at least one OH, NH and/or NH$_2$ group.

When the polymer is a polyurethane it is preferably amine quenched. When the polymer is a polyurethane it is preferably contains dimethylol propionic acid units to increase solubility.

Synthesis of several suitable dye-polymers is discussed, for example, in WO 2011/047987, WO 2012/130492, WO 2012/126987, WO 2012/098046 or WO 2012/126665, the disclosure of which is hereby incorporated in their entirety.

In certain embodiments the polymers may be alkoylated to aid solubility, more preferably ethoxylated or propoxylated, most preferably ethoxylated.

Also suitable are backbones derived from biopolymers such as proteins and polysaccharides. Preferred polysaccharides are anionic polysaccharides such as carrageenan, alginate or a mixture thereof. Preferred proteins are milk proteins. Milk proteins are whey protein (such as lactoglubulin and/or lactalbumin) and caseinate and mixtures of these.

Preferably, each polymer backbone should be covalently bound to at least one dye molecule.

Preferably the dye-polymer contains 0.5 to 50% dye substituent by total weight of the polymer, more preferably 1 to 20%. Additionally or alternatively it is preferred that the mol ratio of dye substituent:polymer backbone is greater than or equal to 1:1, more preferably 2:1 to 1000:1.

Suitable reactive dyes for covalent binding to the polymer backbone are described, for example, in "Industrial Dyes" (K. Hunger ed, Wiley VCH 2003). Many Reactive dyes are listed in the colour index (Society of Dyers and Colourists and American Association of Textile Chemists and Colorists). Reactive dyes consist of a chromophore covalently attached to a reactive group. The chromophore provides visible colour and the reactive group provides a group which can be covalently bound to the polymer backbone. The reactive dye has a maximum extinction coefficient in the range 400 to 700 nm of greater than 1000, preferably greater than 10000 L/mol/cm.

Reactive groups are preferably selected from heterocyclic reactive groups and, a sulfooxyethylsulfonyl reactive group (—SO$_2$CH$_2$CH$_2$OSO$_3$Na), which is converted to a vinylsulfone in alkali. The heterocyclic reactive groups are preferably nitrogen contains aromatic rings bound to a halogen or an ammonium group or a quaternary ammonium group which react with NH$_2$ or NH groups of the polymers to form covalent bonds. The halogen is preferred, most preferably Cl or F.

Preferably, the reactive dye comprises a reactive group selected from dichlorotriazinyl, difluorochloropyrimidine, monofluorotrazinyl, dichloroquinoxaline, vinylsulfone, difluorotriazine, monochlorotriazinyl, bromoacrlyamide and trichloropyrimidine.

Reactive dyes are preferably sulphonated.

The reactive group may be linked to the dye chromophore via an alkyl spacer for example: dye-NH—CH$_2$CH$_2$-reactive group.

Especially preferred heterocylic reactive groups are

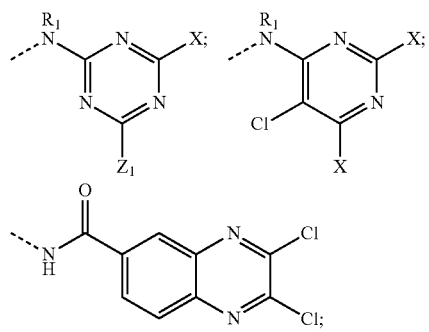

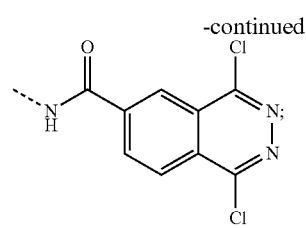

Wherein R$_1$ is selected from H or alkyl, preferably H.

X is selected from F or Cl

When X=Cl, Z$_1$ is selected from —Cl, —NR$_2$R$_3$, —OR$_2$, —SO$_3$Na,

When X=F, Z$_1$ is preferably selected from —NR$_2$R$_3$

R$_2$ and R$_3$ are independently selected from H, alkyl and aryl groups. Aryl groups are preferably phenyl and are preferably substituted by —SO$_3$Na or —SO$_2$CH$_2$CH$_2$OSO$_3$Na. Alkyl groups are preferably methyl or ethyl and may be substituted by SO$_2$CH$_2$CH$_2$OSO$_3$Na.

The phenyl groups may be further substituted with suitable uncharged organic groups, preferably with a molecular weight lower than 200. Preferred groups include —CH$_3$, —C$_2$H$_5$, and —OCH$_3$.

The alkyl groups may be further substituted with suitable uncharged organic groups, preferably with a molecular weight lower than 200. Preferred groups include —CH$_3$, —C$_2$H$_5$, —OH, —OCH$_3$, —OC$_2$H$_4$OH.

Most preferred heterocylic reactive groups are selected from

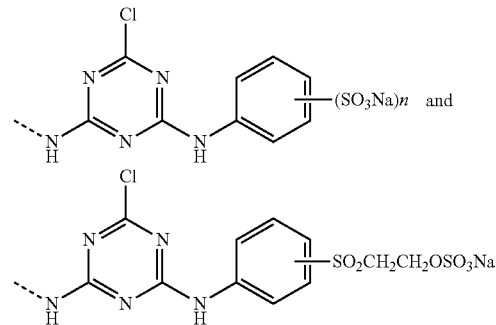

Where n=1 or 2, preferably 1.

Preferably the reactive dye contains more than one reactive group, preferably two or three.

Preferably, the reactive dye comprises a chromophore selected from azo, anthraquinone, phthalocyanine, formazan and triphendioaxazine, most preferably a mono-azo, bis-azo and anthraquinone chromophore.

Where the dye is an azo dye it is preferred that the azo dye is not an azo-metal complex dye.

Preferably the reaction of the polymer backbone and the reactive dye to form the dye polymers, takes place in water at alkaline pH, preferable pH=10 to 11.5, at temperature of 40-100° C. for 1 to 3 hours after the dye is added to the solution. Thereafter the solution is cooled to room temperature and neutralised to pH=7 within 1 to 2 hours. The level of polymer backbone in the reaction solution is preferable from 2 to 50 wt %, more preferably from 5 to 20 wt %. These conditions minimise the production of hydrolysed dye, which is not covalently attached to the polymer backbone.

Examples of the chemical binding reaction between the polymer backbone and reactive dye are shown below.

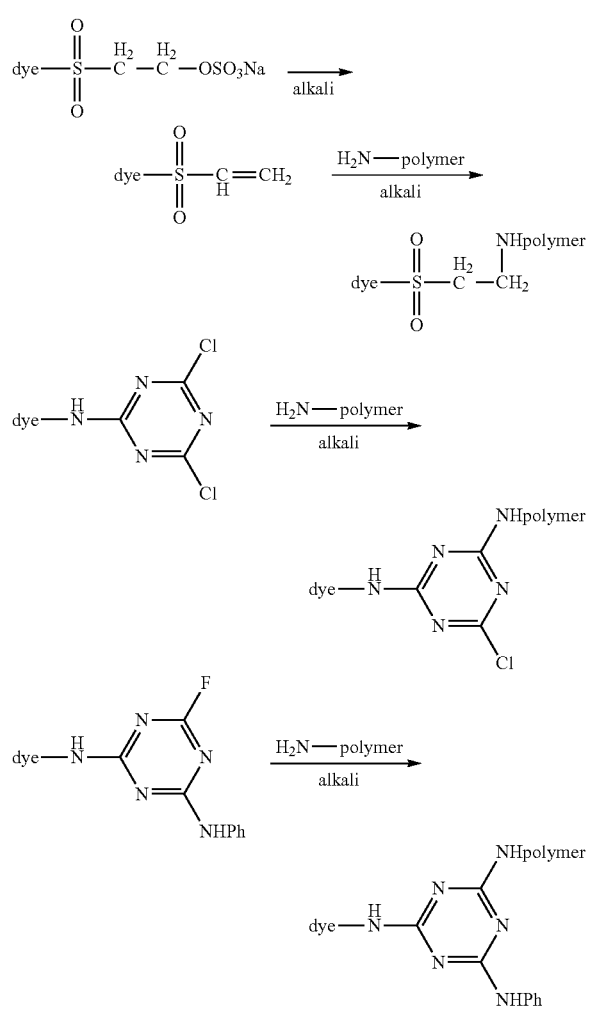

Hydrolysed dye is formed when the reactive dye reacts with water rather than the polymer. Hydrolysed dye is preferably absent and may be removed by careful control of the reaction condition or by separation techniques such as dialysis or preparative chromatography. Preferably there is less than 100 ppm, more preferably less than 5 ppm, most preferably from 0 to 1 ppm, of hydrolysed reactive dye per 1000 ppm of dye polymer (backbone+substituent).

Examples of reactive dyes include reactive black 5, reactive blue 19, reactive red 2, reactive blue 171, reactive red 84, reactive red 66, reactive red 141, reactive red 239, reactive blue 269, reactive blue 11, reactive yellow 17, reactive orange 4, reactive orange 16, reactive green 19, reactive brown 2, reactive brown 50, Procion Red Brown HEXL, Procion Navy HEXL, Levafix Yellow CA, Levafic Amber CA, Levafix Orange CA, Levafix Fast Red CA.

The preferred dyes are red, pink or purple dyes as the compositions of the present invention have been found to be especially suitable for providing skin with an attractive pinkish colour.

Red dyes are most preferred, especially Reactive Red dyes. Reactive Red dyes are preferably selected from monoazo and bis-azo dyes.

A preferred reactive red azo dye is of the form

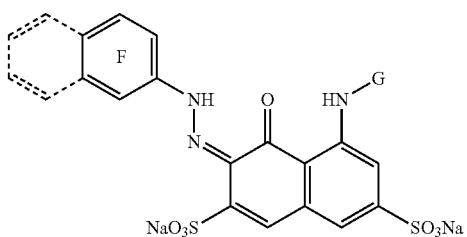

Where the F ring is optionally extended to form a naphthyl group and is optionally substituted by groups selected from sulphonate groups ($SO_3Na$) and a reactive group. G is selected from a reactive group, H, or alkyl group. A reactive group must be present on the dye.

Examples of reactive red dyes are reactive red 2, reactive red 3, reactive red 4, reactive red 8, reactive red 9, reactive red 12, reactive red 13, reactive red 17, reactive red 22, reactive red 24, reactive red 29, reactive red 33, reactive red 66, reactive red 66, reactive red 139, reactive red 198, reactive red 141, reactive red 239, or mixtures of two or more of these.

The present inventors have found that for skin care applications where natural skin tones are preferred, it is necessary to limit the amount of dye polymer in the composition. The inventors also found that even at such low levels natural skin tone (such as pinkishness) could be enhanced and in some instances persist even after washing. Thus the skin care composition comprises the dye polymer in an amount of from 0.00001 to 0.1% by weight of the composition, more preferably from 0.0001 to 0.07%, more preferably still from 0.0005 to 0.05%, even more preferably from 0.001 to 0.02%, and most preferably from 0.004 to 0.01%. By the term 'an amount' is meant that the composition comprises a total amount in the composition. The composition may comprise one or more dye polymers but the 'amount' as mentioned above is the total amount of dye polymer present in the composition. In the foregoing amounts, the dye polymer is expressed in terms of amount of reactive dye substituent by weight of the skin care composition. For example, if a skin care composition comprises 0.1% by weight of total dye polymer (backbone+substituent) and the polymer comprises 20 wt % substituent and 80 wt % backbone by total weight of the polymer, then the amount of dye polymer will be expressed as 0.02% by total weight of the composition.

The polymer is preferably present in the composition as a solute and is thus preferably not substantially in particulate form or absorbed to particulate matter in the composition.

The composition of the present invention preferably comprises opacifying particles as such particles assist for example in providing skin benefits such as whitening and masking blemishes. These are particles with very high refractive index, i.e., having a refractive index of at least 1.7. For example the opacifying particles may have a refractive index of greater than 1.8, more preferably greater than 1.9 and most preferably from 2.0 to 2.7. Refractive index values referred to herein are those determined at a temperature of 25° C. and a wavelength of 589 nm unless otherwise stated.

Examples of such opacifying particles are those comprising bismuth oxy-chloride, boron nitride, titanium dioxide, zirconium oxide, aluminium oxide, zinc oxide or combinations thereof. More preferred are opacifying particles comprising zinc oxide, zirconium oxide, titanium dioxide or a combination thereof as these materials have especially high refractive index. Most preferred are opacifying particles comprising titanium dioxide. Preferably the composition comprises opacifying particles in an amount of from 0.001 to 10%, more preferably 0.01 to 7%, more preferably still 0.02 to 5% and most preferably 0.05 to 2% by weight of the skin care composition.

Opacifying particles are preferably micronized. Preferably the opacifying particles have a primary particle size in the range of from 20 to 2000 nm, and more preferably from 25 to 900 nm, and most preferably, from 30 to 400 nm, including all ranges subsumed therein. Herein "primary particle size" means the size (diameter) measurable by transmission electron microscopy (TEM) using a method such as that described by S. Gu et al in *Journal of Colloid and Interface Science*, 289 (2005) pp. 419-426. In the event that a particle is not spherical then "diameter" means the largest distance measurable across the particle.

The opacifying particles are typically separate from the dye polymer (i.e., the composition comprises dye polymer and additionally comprises the opacifying particles). The opacifying particles are typically compounded in the composition at a higher level than the dye polymer. For example, the composition preferably comprises the opacifying particles and dye polymer in a weight ratio (opacifying particles:dye polymer) of from 1000:1 to 1:1, more preferably 100:1 to 1.1:1, more preferably still from 50:1 to 1.5:1 and most preferably from 20:1 to 2:1, wherein amount of dye polymer is in terms of total dye polymer (i.e. backbone+ substituent).

Compositions of the present invention will also include a cosmetically acceptable carrier. In some embodiments the carrier will be (or at least comprise) a water and oil emulsion, which in certain embodiments may be water-in-oil emulsion. Preferred emulsions, however, are the oil-in-water variety. Where the carrier is an emulsion, it is preferred that the dye polymer is dispersed in the aqueous phase of the water and oil emulsion.

Preferred hydrophobic material for use in the oil phase of such emulsions includes emollients such as fats, oils, fatty alcohols, fatty acids, soaps, silicone oils, synthetic esters and/or hydrocarbons. Many organic sunscreens are also hydrophobic materials and may be used alone or in combination with one or more of the foregoing emollients.

Silicones may be divided into the volatile and nonvolatile variety. Volatile silicone oils (if used) are preferably chosen from cyclic (cyclomethicone) or linear polydimethylsiloxanes containing from 3 to 9, preferably from 4 to 5, silicon atoms.

Nonvolatile silicones useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5\times10^{-6}$ to 0.1 m$^2$/s at 25° C. Among the preferred nonvolatile emollients useful in the present compositions are the polydimethyl siloxanes having viscosities from about $1\times10^{-s}$ to about $4\times10^{-4}$ m$^2$/s at 25° C.

Organopolysiloxane crosspolymers can be usefully employed. Representative of these materials are dimethicone/vinyl dimethicone crosspolymers and dimethicone crosspolymers available from a variety of suppliers including Dow Corning (9040, 9041, 9045, 9506 and 9509), General Electric (SFE 839), Shin Etsu (KSG-15, 16 and 18 [dimethicone/phenyl vinyl dimethicone crosspolymer]), and Grant Industries (Gransil brand of materials), and lauryl dimethicone/vinyl dimethicone crosspolymers supplied by Shin Etsu (e.g. KSG-31, KSG-32, KSG-41, KSG-42, KSG-43 and KSG-44).

Specific examples of non-silicone emollients include stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate, and mixtures thereof.

Among the ester emollients are:
a) Alkenyl or alkyl esters of fatty acids having 10 to 20 carbon atoms. Examples thereof include isoarachidyl neopentanoate, isodecyl neopentanoate, isononyl isononanoate, cetyl ricinoleate, oleyl myristate, oleyl stearate, and oleyl oleate;
b) Ether-esters such as fatty acid esters of ethoxylated fatty alcohols;
c) Polyhydric alcohol esters. Butylene glycol, ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols. Exemplative is pentaerythrityl tetraethylhexanoate;
d) Wax esters such as beeswax, spermaceti wax and tribehenin wax;
e) Sterols esters, of which cholesterol fatty acid esters are examples thereof;
f) Sugar ester of fatty acids such as sucrose polybehenate and sucrose polycottonseedate; or
g) mixtures of two or more of the foregoing (a) to (f).

Of particular use also are the $C_{12-15}$ alkyl benzoate esters sold under the Finsolve brand.

Hydrocarbons which are suitable emollients include petrolatum, mineral oil, $C_{11}$-$C_{13}$ isoparaffins, polyalphaolefins, isohexadecane or a mixture thereof.

In a particularly preferred embodiment, the hydrophobic material comprises 1 to 25% fatty acid or 0.1 to 80% soap by weight of the composition. Mixtures of fatty acid and soap are also suitable e.g. vanishing cream base which gives a highly appreciated matty feel to the skin. C12 to C20 fatty acids are especially preferred for the present invention, more preferred being C14 to C18 fatty acids. The most preferred fatty acid is stearic acid, palmitic acid or a mixture thereof. The fatty acid in the composition is more preferably present in an amount in the range of 5 to 20% by weight of the composition. Soaps can include alkali metal salt of fatty acids, like sodium or potassium salts, most preferred being potassium stearate. The soap is preferably present in an amount in the range of 0.1 to 10%, more preferably 0.5 to 3% by weight of the composition. Generally a vanishing cream base in skin care compositions is prepared by taking a desired amount of total fatty matter and mixing with potassium hydroxide in desired amounts. The soap is usually formed in-situ during the mixing.

Amounts of water in the carrier may, for example, range from 1 to 99%, more preferably from 5 to 90%, even more preferably from 35 to 80%, optimally between 40 and 70% by weight of the skin care composition.

The composition of the invention preferably comprises a skin lightening agent. The skin lightening agent is preferably chosen from one or more of a vitamin B3 compound or its derivative e.g. niacin, nicotinic acid or niacinamide or other well known skin lightening agents e.g. adapalene, aloe extract, ammonium lactate, anethole derivatives, apple extract, arbutin, azelaic acid, kojic acid, bamboo extract, bearberry extract, bletilla tuber, bupleurum falcatum extract, burnet extract, butyl hydroxy anisole, butyl hydroxy toluene, citrate esters, Chuanxiong, Dang-Gui, deoxyarbutin, 1,3-diphenyl propane derivatives, 2,5-dihydroxybenzoic acid and its derivatives, 2-(4-acetoxyphenyl)-1,3-dithane, 2-(4-hydroxyphenyl)-1,3-dithane, ellagic acid, escinol, estragole derivatives, Fadeout (Pentapharm), Fangfeng, fennel extract, ganoderma extract, gaoben, Gatuline Whitening (Gattlefosse), genistic acid and its derivatives, glabridin and its derivatives, gluco pyranosyl-1-ascorbate, gluconic acid, glycolic acid, green tea extract, 4-hydroxy-5-methyl-3[2H]-furanone, hydroquinone, 4-hydroxyanisole and its derivatives, 4-hydroxy benzoic acid derivatives, hydroxycaprylic acid, inositol ascorbate, lemon extract, linoleic acid, magnesium ascorbyl phosphate, Melawhite (Pentapharm), morus alba extract, mulberry root extract, 5-octanoyl salicylic acid, parsley extract, phellinus linteus extract, pyrogallol derivatives, 2,4-resorcinol derivatives, 3,5-resorcinol derivatives, rose fruit extract, salicylic acid, Song-Yi extract, 3,4,5-trihydroxybenzyl derivatives, tranexamic acid, vitamins like vitamin B6, vitamin B12, vitamin C and its derivatives, vitamin A, dicarboxylic acids, resorcinol derivatives (especially 4-substituted resorcinol derivatives), extracts from plants viz. rubia and symplocos, hydroxycarboxylic acids like lactic acid and their salts e.g. sodium lactate, and mixtures thereof. Vitamin B3 compounds (including derivatives of vitamin B3) e.g. niacin, nicotinic acid or niacinamide are the more preferred skin lightening agent as per the invention, most preferred being niacinamide. Vitamin B3 compounds, when used, are preferably present in an amount in the range of 0.1 to 10%, more preferably 0.2 to 5% by weight of the composition.

The composition preferably additionally comprises one or more organic sunscreens. A wide variety of organic sunscreen agents are suitable for use in combination with the essential ingredients of this invention. Suitable UV-A/UV-B sunscreen agents include, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. The most suitable organic sunscreens are 2-ethylhexyl-p-methoxycinnamate, butylmethoxydibenzoylmethane or a mixture thereof.

A safe and effective amount of organic sunscreen may be used in the compositions useful in the subject invention. The composition preferably comprises from 0.1% to 10%, more preferably from 0.1% to 5%, of organic sunscreen agent.

Other materials which can be included in the cosmetically acceptable carrier include solvents, humectants, thickeners and powders. Examples of each of these types of material, which can be used singly or as mixtures, are as follows:

Solvents include ethyl alcohol, isopropanol, acetone, ethylene glycol monoethyl ether, diethylene glycol monobutyl ether, diethylene glycol monoethyl ether and mixtures thereof.

Humectants include those of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range, for example, anywhere from 0.5 to 50%, more preferably between 1 and 15% by weight of the composition. Most preferred is glycerol (also known as glycerin). Amounts of glycerin may range, for example, from 0.5% to 50%, more preferably from 1 to 35%, optimally from 2 to 15% by weight of the composition.

A variety of thickening agents may be included in the compositions. Illustrative but not limiting are stearic acid, Acrylamide/Sodium Acryloyldimethyltaurate Copolymer (Aristoflex AVC), Hydroxyethyl Acrylate/Sodium Acryloyldimethyltau rate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range, for example, from 0.05 to 10%, more preferably from 0.3 to 2% by weight of the composition.

Powders include chalk, talc, Fullers earth, kaolin, starch, gums, colloidal silica sodium polyacrylate, tetraalkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

The composition can be formulated in any known format, more preferred formats being creams or lotions.

The skin care composition of this invention is a composition suitable for topical application to human skin, including leave-on and wash-off products. Preferably the term encompasses a fluid liquid, and particularly a moisturizer rather than a make-up product. Most preferred are leave-on compositions. The term "leave-on" as used with reference to compositions herein means a composition that is applied to or rubbed on the skin, and left thereon. The term "wash-off" as used with reference to compositions herein means a skin cleanser that is applied to or rubbed on the skin and rinsed off substantially immediately subsequent to application.

Packaging for the composition of this invention can be a jar or tube as well as any other format typically seen for cosmetic, cream, washing and lotion type products. The compositions may be applied topically and preferably 1-4 milligrams of composition is applied per square centimeter of skin.

The term "skin" as used herein includes the skin on the face (except eye lids and lips), neck, chest, abdomen, back, arms, under arms, hands, and legs. Preferably "skin" means skin on the face other than eye lids and lips.

The dye polymer and/or composition of the invention preferably delivers a cosmetic benefit to the skin of an individual to which it is topically applied. Examples of cosmetic benefits include providing or enhancing natural skin tone, providing or enhancing pinkish appearance, or a combination thereof.

In a most preferred embodiment the cosmetic benefit is delivered in a durable manner. By "durable manner" is meant that the benefit persists after abrasion and/or washing. Preferably the benefit delivered is durable such that it is still perceivable after flushing treated skin with water (25° C.) for one minute.

The following examples are provided to facilitate an understanding of the invention. The examples are not intended to limit the scope of the claims.

EXAMPLES

For preparation of the dye polymers described below, the following experimental procedure was undertaken: 5 g of the polymer was dissolved in water until the polymer dissolved (30 to 400 ml water dependent upon polymer). To this solution, 1.5 g of Reactive Red 2 was added alongside 0.75 g of potassium carbonate. The solution was left stirring for 20 hours. Following the reaction the product was dialyzed against water (cut-off Mw=14,000) for 72 hours (except for Example 1 wherein dialysis was with cut-off Mw=2000 and for 48 hrs). Water was then removed by rotary evaporation and/or freeze drying. The UV-VIS of the resultant product was taken and the % fixation of the dye to the polymer calculated by comparison to the UV-VIS of the dye alone. If all available dye was fixed to the polymer then the fixation was expressed as 100%, and if none (i.e. no reaction=all dye removed by the dialysis) the fixation was expressed as 0%. Fixation values are typically reliable+/−20%.

Preparative Example 1

A dye polymer was prepared by derivatization of polyethyleneimine (Lupasol G35 ex BASF Mw 2000) with Reactive Red 2. 30 ml of water was used for the reaction. The dye fixation was found to be 100%.

Preparative Example 2

A dye polymer was prepared by derivatization of polyurethane (Luviset® P.U.R. ex BASF) with Reactive Red 2. 30 ml of water was used for the reaction. The dye fixation was found to be 42%.

Preparative Example 3

A dye polymer was prepared by derivatization of Polyquaternium-4 (CELQUAT® ex AkzoNobel) with Reactive Red 2. 300 ml of water was used for the reaction. During the reaction, magnetic stirring was used. After the reaction, HCl was added to the PQ-4 solution to ensure full dissolution. The dye fixation was found to be 63%.

Preparative Example 4

A dye polymer was prepared by derivatization of Polyquaternium-37 with Reactive Red 2. The Polyquarernium 37 was synthesized according to literature procedures. 100 ml of water was used for the reaction. The dye fixation was found to be 51%.

Preparative Example 5

A dye polymer was prepared by derivatization of alginate (CRINSTED® Alginate ex Danisco) with Reactive Red 2. 250 ml of water was used for the reaction. The dye fixation was found to be 26%.

Preparative Example 6

A dye polymer was prepared by derivatization of kappa-carrageenan (CRINSTED® Carrageenan ex Danisco) with Reactive Red 2. 300 ml of water was used for the reaction. The dye fixation was found to be 89%. The carrageenan was first slurried in water, heated to 60° C. to speed dissolution, and then cooled back to room temperature before the addition of Reactive Red 2 and $K_2CO_3$ to begin the derivatization reaction.

Preparative Example 7

A dye polymer was prepared by derivatization of hydroxypropyl methylcellulose (HPMC4000 ex Shin-Etsu) with Reactive Red 2. 400 ml of water was used for the reaction. The dye fixation was found to be 100%.

Preparative Example 8

A dye polymer was prepared by derivatization of caseinate (sodium caseinate ex Adamas) with Reactive Red 2. 250 ml of water was used for the reaction. The dye fixation was found to be 78%.

Preparative Example 9

A dye polymer was prepared by derivatization of lactalbumin (Albumin from milk ex TCl) with Reactive Red 2. 350 ml of water was used for the reaction. The dye fixation was found to be 79%.

Example 10

A vanishing cream base formulation was used as shown in Table 1.

TABLE 1

| Ingredient | % w/w |
| --- | --- |
| Stearic Acid | 17 |
| Niacinamide | 1.25 |

TABLE 1-continued

| Ingredient | % w/w |
|---|---|
| Glycerine | 1 |
| Neutralizing Agent (Base) | 0.48 |
| Cetyl Alcohol | 0.53 |
| Dimethicone | 0.5 |
| Cetostearyl ethylhexanoate (and) Isopropyl myristate | 1 |
| Methyl/propyl paraben | 0.3 |
| Parsol MCX (Ethylhexyl Methoxycinnamate) | 0.75 |
| Parsol 1789 (Butylmethoxy Dibenzoyl Methane) | 0.4 |
| Titanium Dioxide (80 nm)[1] | 0.6 |
| Titanium Dioxide (400-700 nm)[2] | 0.1 |
| Minors[3] | 1.05 |
| Water | To 100 |

[1]MT700Z = Titanium Dioxide (and) Stearic Acid (and) Aluminium Hydroxide supplied by TAYCA - size in brackets is primary particle size
[2]SA-TR-10 = Titanium Dioxide (and) Dimethylpolysiloxane supplied by Miyoshi Kasei Inc. - size in brackets is primary particle size.
[3]Minors include vitamins, perfumes, sequestrants, bacteriacides and other skin benefit agents.

To portions of this base formulation were added either the dye polymers as described in Examples 1-9 or red iron oxide pigment (0.03 wt %). In the case of the dye polymers of Examples 1-9 each was added in an amount sufficient to provide 0.03 wt % Reactive Red 2 dye in the formulation. For example, for Carrageenan-RR2 (Example 6) was calculated to contain approximately 20 wt % RR2 substituent by total weight of the polymer. Therefore 0.15 wt % of Carrageenan-$RR_2$ was added to the formulation in order to provide the 0.03 wt % Reactive Red 2 dye in the final formulation.

The resulting skin care products were then tested using the following protocol:
1. Pig skin preparation: Pig skin from towards the back part was bought as food waste from a food market. Excess subcutaneous fat and hair were removed. Then the skin was cut into 3×2 cm² pieces for experiments;
2. Screen test experiment:
   a. Pig skin was cleaned with 0.1 g facial foam to remove the extra fat on the surface and extra water was removed with paper tissue. An image of the skin was taken using a Digieye (Verivide) Imaging System
   b. 12 mg of vanishing cream was massaged into a portion of pigskin for 30 s. A photo was then taken by Digieye 1 min after cream application.
   c. The treated pig skin was washed again with 0.1 g facial foam with 30 s massage and extra water was removed with paper tissue. An image of the skin was taken using a Digieye (Verivide) Imaging System The colour of the skin was measured from the images of the skin and expressed as the CIE L*a*b* values. The L* represent the lightness (100=white, 0=black), a* is the green (−ve values) to red axis (+ve values) and b* is the blue (−ve values) to yellow axis (+ve values). The change in lightness and red-green colour before and after application of the cream was calculated as:

$$L=L(\text{before})-L(\text{after})$$

$$a=a(\text{before})-a(\text{after})$$

A positive •L indicates a darkening of the skin. A positive •a indicates a reddening of the skin. For deposition of a red colour an increase in •L and •a would be expected.

The results are shown in Table 2. Values quoted are the mean of 3 measurements along with the associated 95% confidence intervals.

TABLE 2

| Colourant | •L on application | •L after washing | •a on application | •a after washing |
|---|---|---|---|---|
| None | −0.19 ± 0.31 | −0.39 ± 0.28 | −0.40 ± 0.07 | −0.34 ± 0.12 |
| Example 1 | 0.90 ± 0.17 | −0.30 ± 0.19 | 1.90 ± 0.60 | 0.10 ± 0.12 |
| Example 2 | 2.08 ± 0.15 | 1.89 ± 0.53 | 4.93 ± 0.60 | 4.55 ± 1.11 |
| Example 3 | 2.64 ± 0.20 | 2.44 ± 0.35 | 5.34 ± 0.36 | 5.08 ± 0.11 |
| Example 4 | 0.99 ± 0.19 | 0.37 ± 0.65 | 2.72 ± 0.66 | 1.64 ± 0.43 |
| Example 5 | 2.47 ± 0.11 | 2.35 ± 0.19 | 5.33 ± 0.33 | 5.25 ± 0.24 |
| Example 6 | 2.51 ± 0.49 | 2.72 ± 0.35 | 5.66 ± 0.46 | 5.91 ± 0.79 |
| Example 7 | 1.84 ± 0.23 | 1.47 ± 0.52 | 4.10 ± 0.25 | 3.36 ± 0.40 |
| Example 8 | 1.83 ± 0.54 | 1.48 ± 0.18 | 4.45 ± 0.07 | 3.35 ± 0.28 |
| Example 9 | 1.98 ± 0.17 | 1.49 ± 0.57 | 4.45 ± 0.29 | 3.67 ± 0.74 |
| Pigment | 0.36 ± 0.41 | 0.13 ± 0.45 | 0.78 ± 0.23 | 0.00 ± 0.28 |

The data shows that the dye-polymers provide colour to the skin. The colour is substantive to further washing, as indicated by the similar •a values on application and after washing. The reference pigment provides less colour to the skin (smaller •a value) and washes off, with the •a returning to zero on washing.

The invention claimed is:
1. A skin care composition for topical application and enhancing skin characteristics comprising:
   a) water-soluble dye polymer comprising polymer backbone having negatively charged reactive dye substituent covalently bound thereto;
   b) cosmetically acceptable carrier capable of being topically applied to skin; wherein the dye polymer is present in amount of 0.00001 to 0.1% in terms of reactive dye substituent by weight of the skin care composition, and the polymer backbone of the water-soluble dye polymer is derived from polyethyleneimine, polysaccharide, polyurethane or a polymer having the INCI designation Polyquatemium, and
   c) skin lightening agent, wherein the skin lightening agent comprises vitamin B3 compound,
   the composition being a leave-on composition.
2. The skin care composition as claimed in claim 1 wherein the reactive dye substituent comprises one or more reactive groups selected from dichlorotriazinyl, difluorochloropyrimidine, monofluorotrazinyl, dichloroquinoxaline, vinylsulfone, difluorotriazine, monochlorotriazinyl, bromoacrylamide and trichloropyrimidine.

3. The skin care composition as claimed in claim 1 in which the reactive dye substituent comprises one or more chromophores selected from azo, anthraquinone, phthalocyanine, formazan and triphendioxazine.

4. The skin care composition as claimed in claim 1 wherein the reactive dye substituent is sulphonated.

5. The skin care composition as claimed in claim 1 wherein the polymer backbone is derived from a polysaccharide.

6. The skin care composition as claimed in claim 5 wherein the polymer backbone is derived from anionic polysaccharide selected from carrageenan, alginate or a mixture thereof.

7. The skin care composition according to claim 5 wherein the polysaccharide is an anionic polysaccharide.

8. The skin care composition as claimed in claim 1 wherein the polymer backbone is derived from a polymer having the designation Polyquaternium.

9. The skin care composition as claimed in claim 8 wherein the polyquaternium is Polyquaternium-4 or Polyquaternium-37.

10. A method for delivering a cosmetic benefit comprising the step of topically applying the composition of claim 1, the cosmetic benefit selected from providing or enhancing natural skin tone, providing or enhancing pinkish appearance, or a combination thereof.

11. A method for delivering a cosmetic benefit comprising the step of topically applying a water-soluble dye polymer in a leave-on skin composition, the cosmetic benefit selected from providing or enhancing natural skin tone, providing or enhancing pinkish appearance, or a combination thereof wherein the dye polymer comprises polymer backbone having negatively charged reactive dye substituent covalently bound thereto, where the leave-on skin composition comprises:

a) the water-soluble dye polymer comprising polymer backbone having negatively charged reactive dye substituent covalently bound thereto;

b) cosmetically acceptable carrier capable of being topically applied to skin; wherein the dye polymer is present in amount of 0.00001 to 0.1% in terms of reactive dye substituent by weight of the skin care composition, and the polymer backbone of the water-soluble dye polymer is derived from polyethyleneimine, polysaccharide, polyurethane or a polymer having the INCI designation Polyquatemium, and c) skin lightening agent, wherein the skin lightening agent comprises vitamin B3 compound.

* * * * *